US00RE50875E

(19) United States
(12) Reissued Patent
Jungong et al.

(10) Patent Number: US RE50,875 E
(45) Date of Reissued Patent: Apr. 28, 2026

(54) PROCESSES FOR PRODUCING HIGH-PURITY TRIFLUOROIODOMETHANE

(71) Applicant: Honeywell International Inc., Charlotte, NC (US)

(72) Inventors: Christian Jungong, Depew, NY (US); Daniel C. Merkel, Orchard Park, NY (US); Haiyou Wang, Amherst, NY (US); Terris Yang, East Amherst, NY (US); Pascal Bolomey, Solon, OH (US)

(73) Assignee: Solstice Advanced Materials US, Inc., Wilmington, DE (US)

(21) Appl. No.: 18/118,955

(22) Filed: Mar. 8, 2023

Related U.S. Patent Documents

Reissue of:
(64) Patent No.: 10,941,091
Issued: Mar. 9, 2021
Appl. No.: 16/683,924
Filed: Nov. 14, 2019

U.S. Applications:
(60) Provisional application No. 62/774,520, filed on Dec. 3, 2018.

(51) Int. Cl.

| | |
|---|---|
| ***C07C 17/389*** | (2006.01) |
| ***B01D 3/14*** | (2006.01) |
| ***B01D 53/04*** | (2006.01) |
| ***B01D 53/14*** | (2006.01) |
| ***B01J 20/08*** | (2006.01) |

(52) U.S. Cl.
CPC ..... *C07C 17/389* (2013.01); *B01D 3/143* (2013.01); *B01D 53/04* (2013.01); *B01D 53/1456* (2013.01); *B01D 53/1493* (2013.01); *B01J 20/08* (2013.01)

(58) Field of Classification Search
CPC ..... C07C 17/389; C07C 17/395; C07C 17/38; C07C 19/16; B01D 3/143; B01D 53/04; B01D 53/1456; B01D 53/1493; B01D 15/00; B01D 53/02; B01D 53/40; B01D 2251/30; B01D 2251/604; B01D 2251/606; B01D 2253/104; B01D 2257/2068; B01D 2257/80; B01D 3/009; B01D 53/70; B01J 20/08; Y02P 20/10; Y02P 20/151
See application file for complete search history.

(56) References Cited

U.S. PATENT DOCUMENTS

| | | | |
|---|---|---|---|
| 3,381,041 | A | 4/1968 | Yutaka et al. |
| 5,892,136 | A | 4/1999 | Nagasaki et al. |
| 8,058,486 | B2 | 11/2011 | Merkel et al. |
| 8,766,020 | B2 | 7/2014 | Wang et al. |
| 8,987,536 | B2 | 3/2015 | Sun et al. |
| 9,447,004 | B2 | 9/2016 | Wang et al. |
| 9,463,432 | B2 | 10/2016 | Tung et al. |
| 10,125,066 | B1 | 11/2018 | Jungong et al. |
| 2006/0129006 | A1 | 6/2006 | Mukhopadhyay et al. |
| 2008/0011159 | A1 | 1/2008 | Thomas et al. |
| 2008/0108854 | A1 | 5/2008 | Yang et al. |
| 2010/0029997 | A1 | 2/2010 | Wang et al. |
| 2012/0184785 | A1 | 7/2012 | Cottrell et al. |
| 2017/0001931 | A1* | 1/2017 | Wang ..... C07C 21/18 |
| 2020/0172457 | A1 | 6/2020 | Jungong et al. |

FOREIGN PATENT DOCUMENTS

| | | | | |
|---|---|---|---|---|
| CN | 105503515 | A | 4/2016 | |
| CN | 107176902 | * | 9/2017 | ..... C07C 17/38 |
| CN | 107176902 | A | 9/2017 | |
| CN | 108246277 | A * | 7/2018 | |
| CN | 108675914 | A | 10/2018 | |
| EP | 1918268 | A2 | 5/2008 | |
| ES | 2370256 | T3 | 12/2011 | |
| GB | 2547277 | A | 8/2017 | |
| KR | 10-2004-0043774 | A | 5/2004 | |
| WO | 2013/049742 | A1 | 4/2013 | |
| WO | 2015/053339 | A1 | 4/2015 | |
| WO | 2017/013405 | A1 | 1/2017 | |
| WO | 2017/031046 | A1 | 2/2017 | |

OTHER PUBLICATIONS

English translation of CN 108675914 A to Dong, Oct. 19, 2018. (Year: 2018).*
International Search Report and Written Opinion received for PCT Patent Application No. PCT/US2018/055433, mailed on Mar. 22, 2019, 6 pages.
International Search Report and Written Opinion received for PCT Patent Application No. PCT/US2019/064143, mailed on Mar. 30, 2020, 7 pages.
Hwahak Konghak "Synthesis of CF3I by Direct Iodination of CF3COOH on Solid Catalyst", Journal of the Korean Institute of Chemical Engineers, vol. 39, No. 2, Apr. 2021, pp. 144-149 (With English Translation of Abstract).
U.S. Appl. filed Nov. 2, 2016, 17 pages., U.S. Appl. No. 62/416,206.

* cited by examiner

*Primary Examiner* — Alan D Diamond
(74) *Attorney, Agent, or Firm* — Faegre Drinker Biddle & Reath LLP

(57) ABSTRACT

The present disclosure provides a method for purifying trifluoroiodomethane. The method includes providing a process stream comprising trifluoroiodomethane, organic impurities, and acid impurities; reacting the process stream with a basic aqueous solution, the basic aqueous solution comprising water and at least one base selected from the group of an alkali metal carbonate and an alkali metal hydroxide; and separating at least some of the organic impurities from the process stream.

25 Claims, 2 Drawing Sheets

PROCESSES FOR PRODUCING HIGH-PURITY TRIFLUOROIODOMETHANE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application *is a broadening reissue application of and claiming priority to U.S. Pat. No. 10,941,091, entitled Processes for Producing High-Purity Trifluoroiodomethane, issued Mar. 9, 2021, which* claims priority to U.S. Provisional Application No. 62/774,520, filed Dec. 3, 2018, *the entire disclosures of* which [is] *are* herein incorporated by reference [in its entirety].

FIELD

The present disclosure relates to processes for producing high-purity trifluoroiodomethane ($CF_3I$). Specifically, the present disclosure relates to processes for purifying trifluoroiodomethane resulting in high yields of high-purity trifluoroiodomethane.

BACKGROUND

Trifluoroiodomethane ($CF_3I$), also known as perfluoromethyliodide, trifluoromethyl iodide, or iodotrifluoromethane, is a useful compound in commercial applications as a refrigerant or a fire suppression agent, for example. $CF_3I$ is a low global warming potential molecule with almost no ozone depletion potential. $CF_3I$ can replace more environmentally damaging materials.

There are several known processes for producing $CF_3I$ and compositions including $CF_3I$. Many of these processes involve the direct catalytic iodination of a suitable precursor compound containing a $CF_3$ group moiety. In many of these processes, a crude process stream including the $CF_3I$ may also include organic impurities, acid impurities, and water. The organic impurities may include fluorinated and iodinated hydrocarbons such as pentafluoroethane (HFC-125), hexafluoropropene (HFO-1216), 1,1,1,2,3,3,3-heptafluoropropane (HFC-227ea), 1,1,3,3,3-pentafluoropropene (HFO-1225zc), 1,1,1,3,3,3-hexafluoropropane (HFC-236fa), and/or methyl iodide ($CH_3I$), for example. The organic impurities may also include carbon dioxide ($CO_2$). The organic impurities may be formed as byproducts during the production of the $CF_3I$ and/or may be present in the reactants or other starting materials used to produce the $CF_3I$.

$CH_3I$ exhibits moderate-to-high acute toxicity for inhalation and ingestion, according to the U.S. Department of Agriculture. The specification for $CH_3I$ in high-purity $CF_3I$ needed for toxicity assessment is less than 5 ppm. The concentration of $CH_3I$ in the crude process stream may typically be about 1,000 ppm, and may be as high as 5,000 ppm.

The acid impurities may include hydrogen fluoride (HF), hydrogen chloride (HCl), hydrogen iodide (HI), and/or trifluoroacetic acid (TFA), for example. The acid impurities may be formed as byproducts during the production of the $CF_3I$ and/or may be present in the reactants or other starting materials used to produce the $CF_3I$. The concentration of acid impurities in the crude process stream may range from about 20 ppm to about 100 ppm. The water may also be present in the reactants or other starting materials used to produce the $CF_3I$. The concentration of water in the crude process stream may range from about 5 ppm to about 100 ppm. The presence of the acid impurities and water in the crude process stream creates a corrosive medium which may have detrimental effects on downstream processing equipment, such as distillation columns, pumps, piping, sensors, storage tanks, etc. The corrosion resulting in replacement and/or repair of the equipment may reduce the overall efficiency of the purification processes. High-purity $CF_3I$ must have no more than 1 ppm of acid impurities and no more than 10 ppm water.

Thus, there is a need for purification processes that remove enough of the organic impurities (especially $CH_3I$), acid impurities and water to produce high-purity $CF_3I$.

SUMMARY

The present disclosure provides processes for purifying trifluoroiodomethane ($CF_3I$) resulting in high yields of high-purity trifluoroiodomethane.

In one form thereof, the present disclosure provides a method for purifying trifluoroiodomethane. The method includes providing a process stream comprising trifluoroiodomethane, organic impurities, and acid impurities; reacting the process stream with a basic aqueous solution, the basic aqueous solution comprising water and at least one base selected from the group of an alkali metal carbonate and an alkali metal hydroxide; and separating at least some of the organic impurities from the process stream.

In the reacting step, the at least one base may include an alkali metal carbonate. A concentration of the alkali metal carbonate in the basic aqueous solution may be from about 0.01 wt. % to about 20 wt. %. A concentration of the alkali metal carbonate in the basic aqueous solution may be from about 0.5 wt. % to about 5 wt. %. The alkali metal carbonate may include sodium carbonate.

The at least one base may include an alkali metal hydroxide. A concentration of the alkali metal hydroxide in the basic aqueous solution may be from about 0.01 wt. % to about 20 wt. %. A concentration of the alkali metal hydroxide in the basic aqueous solution may be from about 0.5 wt. % to about 1 wt. %. The alkali metal hydroxide may include potassium hydroxide.

In the reacting step, a temperature of the process stream may be from about 5° C. to about 80° C. and a pressure of the process stream may be from about 1 psig to about 100 psig.

In the providing step, the organic impurities may include methyl iodide. The concentration of the methyl iodide in the process stream, in GC area % of total organic compounds, may be reduced by from about 1% to about 70% by the reacting step. The reacting step may precede the separation step. The reacting step may follow the separation step.

The method may further include the additional step of drying to remove at least some of the water from the process stream immediately after the reacting step. After the reacting step, the drying step, and the separation step, the process stream may include at least about 99 wt. % trifluoroiodomethane, less than about 50 ppm methyl iodide, less than about 100 ppm water, and less than about 20 ppm acid impurities. The method may be a continuous process.

In another form thereof, the present disclosure provides a method for purifying trifluoroiodomethane. The method includes providing a process stream comprising trifluoroiodomethane, organic impurities, and acid impurities; contacting the process stream with an acid reactive agent; and separating at least some of the organic impurities from the process stream.

The acid reactive agent may include an alumina adsorbent. In the contacting step, the process stream may be in a liquid phase and temperature of the process stream may be from about −50° C. to about 50° C. and a pressure of the process stream may from about 1 psig to about 100 psig. In the contacting step, the process stream may be in a gas phase and a temperature of the process stream may be from about −20° C. to about 60° C. and a pressure of the process stream may be from about 1 psig to about 100 psig.

The contacting step may precede the separation step. The contacting step may follow the separation step.

The method may further include the additional step of drying to remove at least some of the water from the process stream immediately after the contacting step. After the contacting step, the drying step, and the separation step, the process stream may include at least about 99 wt. % trifluoroiodomethane, less than about 50 ppm methyl iodide, less than about 100 ppm water, and less than about 20 ppm acid impurities.

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
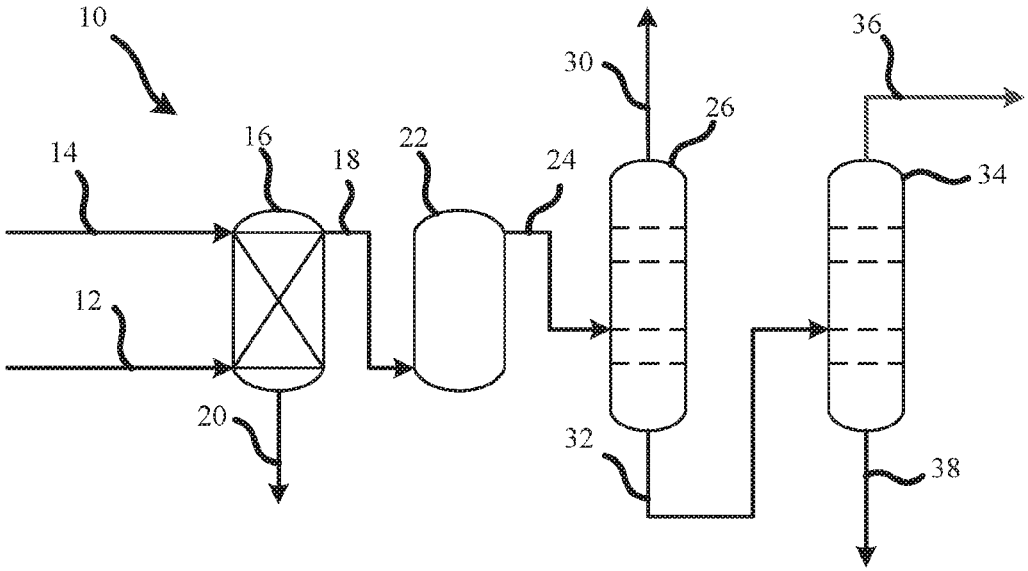
FIG. 1 is a process flow diagram showing a process for producing high-purity trifluoroiodomethane.

The present disclosure provides processes for purifying crude trifluoroiodomethane ($CF_3I$) resulting in high yields of high-purity $CF_3I$. It has been found that the neutralization of acids from process streams including $CF_3I$ is especially challenging because $CF_3I$ may chemically break down when contacted by basic solutions typically used for neutralizing acids, resulting in a loss of $CF_3I$ product.

Acid impurities may be removed from the process stream by passing the process stream through a scrubber containing a basic aqueous solution. It has been found that by passing a crude process stream including $CF_3I$ and acid impurities through the scrubber containing a basic aqueous solution including water and at least one base in defined concentration range, the acid impurities in the process stream may be effectively removed without significant breakdown of $CF_3I$. The base may be an alkali metal carbonate and/or an alkali metal hydroxide.

The basic aqueous solution may consist essentially of water and the at least one base. The basic aqueous solution may consist of water and the at least one base.

The base may comprise an alkali metal hydroxide. The base may consist essentially of an alkali metal hydroxide. The base may consist of an alkali metal hydroxide. The alkali metal hydroxide may be selected from a group consisting of sodium hydroxide (NaOH), potassium hydroxide (KOH), and lithium hydroxide (LiOH), and combinations thereof. Preferably, the alkali metal hydroxide may comprise potassium hydroxide. More preferably, the alkali metal hydroxide may consist essentially of potassium hydroxide. Most preferably, the alkali metal hydroxide may consist of potassium hydroxide. The alkali metal hydroxide may consist essentially of sodium hydroxide. The alkali metal hydroxide may consist of sodium hydroxide. The alkali metal hydroxide may consist essentially of lithium hydroxide. The alkali metal hydroxide may consist of lithium hydroxide.

The crude process stream may also include organic impurities. It has been found that the basic aqueous solutions in which the base comprises alkali metal hydroxide may also remove a significant percentage of the organic impurity $CH_3I$. The $CH_3I$ in the process stream may react with the alkali metal hydroxide in the basic aqueous solution within a scrubber to form methanol and an alkali iodide salt according to Equation 1 below:

$$CH_3I+XOH \rightarrow CH_3OH+XI, \qquad \text{Eq. 1:}$$

wherein XI is potassium iodide, sodium iodide, or lithium iodide. The methanol and the alkali iodide salts are easily soluble in the basic aqueous solution, and thus, removed from the process stream.

It has been found that $CH_3I$ undergoes this reaction of Equation 1 more readily than $CF_3I$. Without wishing to be bound by any theory, it is believed that the difference in reactivity is due, at least in part, to a significantly better solubility of $CH_3I$ in water than of $CF_3I$ in water.

The composition of the organic compounds in the process stream may be measured as by gas chromatography (GC) and gas chromatography-mass spectroscopy (GC-MS) analyses. Graph areas provided by the GC analysis for each of the organic compounds may be combined to provide a GC area percentage (GC area %) of the total organic compounds for each of the organic compounds as a measurement of the relative concentrations of the organic compounds in the process stream.

The concentration of $CH_3I$ in the process stream, in GC area % of total organic compounds, may be reduced by the reacting step in which the basic aqueous solution comprises alkali metal hydroxide by as little as about 1%, about 5%, about 10%, about 15%, about 20%, about 25%, about 30%, or about 35%, or may be as much as about 40%, about 45%, about 50%, about 55%, about 60%, about 65%, about 70%, or about 80%, or within any range defined between any two of the foregoing values, such as about 1% to about 80%, about 5% to about 70%, about 10% to about 65%, about 15% to about 60%, about 20% to about 55%, about 25% to about 50%, about 30% to about 45%, or about 35% to about 40%, for example. Preferably, the concentration of $CH_3I$ in the process stream may be reduced by the reacting step from about 1% to about 70%. More preferably, the concentration of $CH_3I$ in the process stream may be reduced by the reacting step from about 5% to about 50%. Most preferably, the concentration of $CH_3I$ in the process stream may be reduced by the reacting step from about 5% to about 30%.

While the $CH_3I$ may be effectively removed from the process stream by distillation, as described below, removing significant amounts $CH_3I$ by the basic aqueous solution prior to distillation may permit the distillation column to run more efficiently. $CH_3I$ may represent the largest component of the organic impurities in the process stream. Removing a significant portion of the organic impurities ahead of the distillation column may increase the flow rate of the process stream through the distillation column and increase the rate at which high-purity $CF_3I$ may be produced. Alternatively, or additionally, the reduction in organic impurities ahead of the distillation column may permit the use of a smaller distillation column to achieve a desired production rate of high-purity $CF_3I$.

Removing significant amounts $CH_3I$ by the basic aqueous solution after distillation may also permit the distillation column to run more efficiently because distillation column will not have to be operated to produce $CF_3I$ as pure as ultimately required. Removing a significant portion of the organic impurities after distillation may increase the flow rate of the process stream through the distillation column as fewer organic impurities need to be removed. Alternatively, or additionally, the reduction in organic impurities after the distillation column may permit the use of a smaller distillation column to achieve a desired production rate of high-purity $CF_3I$.

It has also been found that at higher concentrations of the alkali metal hydroxide, the $CF_3I$ may react with the alkali metal hydroxide in the basic aqueous solution within the scrubber and break down to form carbonyl fluoride, an alkali fluoride salt, an alkali iodide salt, and water according to Equation 2 below:

$$CF_3I+2XOH \rightarrow CF_2O+XI+XF+H_2O \qquad \text{Eq. 2:}$$

wherein XI is potassium iodide, sodium iodide, or lithium iodide, and XF is potassium fluoride, sodium fluoride, or lithium fluoride. Thus, the concentration of the alkali metal hydroxide in the basic aqueous solution must be tightly controlled to limit this breakdown of $CF_3I$ and preserve the yield of $CF_3I$ in the purification process.

A concentration of the alkali metal hydroxide, as a percentage of the total weight of the basic aqueous solution, may be as little as about 0.01 weight percent (wt. %), about 0.02 wt. %, about 0.05 wt. %, about 0.1 wt. %, about 0.2 wt. %, about 0.5 wt. %, or about 1 wt. % or as great as about 2 wt. %, about 5 wt. %, about 10 wt. %, about 15 wt. %, or about 20 wt. %, or within any range defined between any two of the foregoing values, such as about 0.01 wt. % to about 20 wt. %, about 0.02 wt. % to about 15 wt. %, about 0.05 wt. % to about 12 wt. %, about 0.1 wt. % to about 10 wt. %, about 0.2 wt. % to about 5 wt. %, about 0.5 wt. % to about 2 wt. %, about 0.5 wt. % to about 5 wt. %, about 0.05 wt. % to about 1 wt. %, about 0.5 wt. % to about 1 wt. %, or about 0.1 wt. % to about 5 wt. % for example. Preferably, the concentration of the alkali metal hydroxide may be from about 0.1 wt. % to about 5 wt. %. More preferably, the concentration of the alkali metal hydroxide may be from about 0.5 wt. % to about 1 wt. %. Most preferably, the concentration of the alkali metal hydroxide may be about 0.5 wt. %.

It has also been found that the basic aqueous solutions in which the base comprises alkali metal carbonate do not remove a significant percentage of the organic impurity $CH_3I$, but do cause less significant breakdown of $CF_3I$. Thus, it may be preferred to employ basic aqueous solutions in which the base comprises alkali metal carbonate rather than alkali metal hydroxide to preserve more of the $CF_3I$, and rely exclusively on a separation process to remove the $CH_3I$ from the process stream, as described below.

The base may comprise an alkali metal carbonate. The base may consist essentially of an alkali metal carbonate. The base may consist of an alkali metal carbonate. The alkali metal carbonate may be selected from a group consisting of sodium carbonate ($Na_2CO_3$), potassium carbonate ($K2CO_3$), and lithium carbonate ($Li2CO_3$), and combinations thereof. Preferably, the alkali metal carbonate may comprise sodium carbonate. More preferably, the alkali metal carbonate may consist essentially of sodium carbonate. Most preferably, the alkali metal carbonate may consist of sodium carbonate. The alkali metal carbonate may consist essentially of potassium carbonate. The alkali metal carbonate may consist of potassium carbonate. The alkali metal carbonate may consist essentially of lithium carbonate. The alkali metal carbonate may consist of lithium carbonate.

A concentration of the alkali metal carbonate, as a percentage of the total weight of the basic aqueous solution, may be as little as about 0.01 weight percent (wt. %), about 0.02 wt. %, about 0.05 wt. %, about 0.1 wt. %, about 0.2 wt. %, about 0.5 wt. %, or about 1 wt. % or as great as about 2 wt. %, about 5 wt. %, about 10 wt. %, about 15 wt. %, or about 20 wt. %, or within any range defined between any two of the foregoing values, such as about 0.01 wt. % to about 20 wt. %, about 0.02 wt. % to about 15 wt. %, about 0.05 wt. % to about 12 wt. %, about 0.1 wt. % to about 10 wt. %, about 0.2 wt. % to about 5 wt. %, about 0.5 wt. % to about 2 wt. %, or about 0.5 wt. % to about 5 wt. %, for example. Preferably, the concentration of the alkali metal carbonate may be from about 0.1 wt. % to about 10 wt. %. More preferably, the concentration of the alkali metal carbonate may be from about 0.5 wt. % to about 5 wt. %. Most preferably, the concentration of the alkali metal carbonate may be about 5 wt. %.

Contact time between the process stream and the basic aqueous solution is not particularly critical and may be as short as 0.5 seconds. Contact time may be much longer and still not cause significant breakdown of $CF_3I$.

The process stream may be in a gas phase or in a liquid phase when passing through the scrubber. Pressure and temperature of the process stream passing through scrubber should be tightly controlled to limit unwanted secondary reactions involving $CF_3I$.

When passing through the scrubber, the process stream may be at a temperature as low as about 5° C., about 10° C., about 15° C., about 20° C., about 25° C., or about 30° C., or as high as about 40° C., about 50° C., about 60° C., about 70° C., or about 80° C., or any temperature within any range defined between any two of the foregoing values, such as about 5° C. to about 80° C., about 10° C. to about 70° C., about 15° C. to about 60° C., about 20° C. to about 50° C., about 25° C. to about 40° C., or about 20° C. to about 40° C., for example. Preferably, the process stream temperature in the scrubber may be from about 10° C. to about 50° C. More preferably, the process stream temperature in the scrubber may be from about 20° C. to about 40° C.

When passing through the scrubber, the process stream may be at a pressure as low as about 1 psig, about 2 psig, about 3 psig, about 5 psig, about 10 psig, about 20 psig, about 25 psig, or about 30 psig, or as high as about 40 psig, about 50 psig, about 60 psig, about 70 psig, about 80 psig, about 90 psig, or about 100 psig, or any pressure within any range defined between any two of the foregoing values, such as about 1 psig to about 100 psig, about 2 psig to about 90 psig, about 3 psig to about 80 psig, about 5 psig to about 70 psig, about 5 psig to about 60 psig, about 5 psig to about 50 psig, about 5 psig to about 40 psig, or about 5 psig to about 50 psig, for example. Preferably, the process stream pressure in the scrubber may be from about 3 psig to about 80 psig. More preferably, the process stream pressure in the scrubber may be from about 5 psig to about 50 psig.

Alternatively, or additionally, acid impurities may be removed from the process stream by passing the process stream through an adsorption column containing an acid active agent. An acid active agent is a material that adsorbs acids.

The acid active agent may comprise at least one adsorbent selected from the group of alumina, alkali metal oxides, alkaline earth metal oxides, metal hydroxides, aluminosilicate minerals, zirconias, and silica. The acid active agent may be an adsorbent selected from the group consisting of alumina, alkali metal oxides, alkaline earth metal oxides, metal hydroxides, aluminosilicate minerals, zirconias, silica, and combinations thereof.

It has been found that by passing the process stream including $CF_3I$ through the adsorption column containing an acid active agent that does not initiate or favor the breakdown of $CF_3I$, the acid impurities in the process stream may be effectively removed without significant yield reduction of $CF_3I$.

The acid active agent may comprise alumina. The acid active agent may consist essentially of alumina. The acid active agent may consist of alumina. The alumina may comprise one or more types of alumina. The alumina may be an activated alumina, such as P-188 or CLR-204 available from UOP LLC, Des Plaines, Ill., HF-200XP from BASF, Iselin, N.J., or aluminum oxide catalyst support from Alfa Aesar, Haverhill, Mass., for example.

Contact time between the process stream and the adsorption column containing the acid active agent is not particularly critical and may be as short as 0.5 seconds. Contact time may be much longer and still not cause significant breakdown of $CF_3I$.

The process stream may be in a gas phase or in a liquid phase when passing through the adsorption column comprising the acid active agent.

When passing through the adsorption column in the liquid phase, the process stream may be at a temperature as low as about −50° C., about −45° C., about −40° C., about −35° C., about −30° C., about −25° C., about −20° C., or about −15° C., or as high as about −10° C., about −5° C., about 0° C., about 5° C., about 10° C., about 15° C., about 20° C., about 25° C., about 30° C., about 35° C., about 40° C., about 45° C., or about 50° C., or any temperature within any range defined between any two of the foregoing values, such as about −50° C. to about 50° C., about −40° C. to about 45° C., about −30° C. to about 40° C., about −25° C. to about 35° C., about −10° C. to about 30° C., or about 0° C. to about −25° C., for example. Preferably, the process stream temperature in the adsorption column may be from about 0° C. to about 35° C. More preferably, the process stream temperature in the adsorption column may be from about 10° C. to about 30° C.

When passing through the adsorption column in the liquid phase, the process stream may be at a pressure as low as about 1 psig, about 5 psig, about 10 psig, about 20 psig, about 25 psig, or about 30 psig, or as high as about 40 psig, about 50 psig, about 60 psig, about 70 psig, about 80 psig, about 90 psig, or about 100 psig, or any pressure within any range defined between any two of the foregoing values, such as about 1 psig to about 100 psig, about 5 psig to about 90 psig, about 10 psig to about 80 psig, about 15 psig to about 70 psig, about 20 psig to about 60 psig, about 25 psig to about 50 psig, about 30 psig to about 40 psig, or about 20 psig to about 50 psig, for example. Preferably, the process stream pressure in the adsorption column may be from about 10 psig to about 90 psig. More preferably, the process stream pressure in the adsorption column may be from about 20 psig to about 50 psig.

When passing through the adsorption column in the gas phase, the process stream may be at a temperature as low as about −20° C., about −15° C., about −10° C., about −5° C., about 0° C., about 5° C., about 10° C., or about 15° C., or as high as about 20° C., about 25° C., about 30° C., about 35° C., about 40° C., about 45° C., about 50° C., about 55° C., or about 60° C., or any temperature within any range defined between any two of the foregoing values, such as about −20° C. to about 60° C., about −10° C. to about 50° C., about 0° C. to about 40° C., about 10° C. to about 30° C., about −5° C. to about 50° C., or about 15° C. to about 40° C., for example. Preferably, the process stream temperature in the adsorption column may be from about −5° C. to about 50° C. More preferably, the process stream temperature in the adsorption column may be from about 15° C. to about 40° C.

When passing through the adsorption column in the gas phase, the process stream may be at a pressure as low as about 1 psig, about 5 psig, about 10 psig, about 20 psig, about 25 psig, or about 30 psig, or as high as about 40 psig, about 50 psig, about 60 psig, about 70 psig, about 80 psig, about 90 psig, or about 100 psig, or any pressure within any range defined between any two of the foregoing values, such as about 1 psig to about 100 psig, about 5 psig to about 90 psig, about 10 psig to about 80 psig, about 15 psig to about 70 psig, about 20 psig to about 60 psig, about 25 psig to about 50 psig, about 30 psig to about 40 psig, or about 20 psig to about 50 psig, for example. Preferably, the process stream pressure in the adsorption column may be from about 10 psig to about 90 psig. More preferably, the process stream pressure in the adsorption column may be from about 15 psig to about 80 psig.

The water may be removed from the process stream by a drying step. The drying step may comprise contacting the process stream with a desiccant. The desiccant may comprise at least one adsorbent selected from the group of anhydrous calcium chloride, anhydrous calcium sulfate, concentrated sulfuric acid, silica, activated charcoal and zeolites. The desiccant may be selected from the group consisting of anhydrous calcium chloride, anhydrous calcium sulfate, concentrated sulfuric acid, silica, activated charcoal, zeolites, and combinations thereof. The desiccant may preferably be a 3 A molecular sieve. It has been found that a 3 A molecular sieve does not initiate or favor the breakdown of $CF_3I$.

It is preferred that the drying step occur immediately after the acid impurities are removed from the process stream. This is so that when the acid impurities are removed from the process stream by passing the process stream through a scrubber containing the basic aqueous solution, water picked up in the scrubber can be removed as well as any moisture present in the crude $CF_3I$ process stream.

When the acid impurities are removed from the process stream by passing the process stream through an adsorption column containing an acid active agent, it is also preferred that the drying step occur immediately after the acid impurities are removed from the process stream. This is so that moisture generated as the acid impurities are removed from the process stream can be removed as well as any moisture present in the crude $CF_3I$ process stream.

The organic impurities may be removed from the process stream by a separation step. The separation step may comprise distilling the process stream. Distilling the process stream may comprise a first distillation and second distillation. The first distillation may remove from the process stream organic impurities having a lower boiling point than $CF_3I$. Such low boiling point organic impurities may include $CO_2$, for example. The second distillation may remove from the process stream organic impurities having a higher boiling point than $CF_3I$. Such high boiling point organic impurities may include $CH_3I$, for example. Separation of $CH_3I$ from the process stream containing $CF_3I$ by distillation may be preferred as the boiling point of $CH_3I$ at standard conditions is 42° C., much higher than the boiling point of $CF_3I$ which is −22° C. at standard conditions.

Alternatively, or additionally, the distilling process may comprise a single distillation in which the organic impurities having a lower boiling point than $CF_3I$ are removed through an overhead stream, followed by the $CF_3I$ through the overhead stream, while the organic impurities having a higher boiling point than $CF_3I$ concentrate in a reboiler.

Distilling of the process stream may be done in either a continuous process or a batch process. The single distillation may be more suitable for a batch process, while the distillation process comprising the first distillation and the second distillation may be more suitable for a continuous process.

The concentration of $CF_3I$ in the purified process stream after reacting with a basic aqueous solution and/or contacting with an acid active agent to remove at least some acid impurities, drying the process stream to remove at least some water, and separating at least some of the organic impurities from the process stream may be greater than about 99 wt. %. Preferably, the concentration of $CF_3I$ in the purified process stream may be greater than about 99.5 wt. %. More preferably, the concentration of $CF_3I$ in the purified process stream may be greater than about 99.9 wt. %. Most preferably, the concentration of $CF_3I$ in the purified process stream may be greater than about 99.99 wt. %.

The concentration of $CH_3I$ in the purified process stream after reacting with a basic aqueous solution and/or contacting with an acid active agent to remove at least some acid impurities, drying the process stream to remove at least some water, and separating at least some of the organic impurities from the process stream may be less than about 50 parts per million (ppm). Preferably, the concentration of $CH_3I$ in the purified process stream may be less than about 20 ppm. More preferably, the concentration of $CH_3I$ in the purified process stream may be less than about 10 ppm. Most preferably, the concentration of $CH_3I$ in the purified process stream may be less than about 5 ppm.

The concentration of acid impurities in the purified process stream after reacting with a basic aqueous solution and/or contacting with an acid active agent to remove at least some acid impurities, drying the process stream to remove at least some water, and separating at least some of the organic impurities from the process stream may be less than about 20 parts per million (ppm). Preferably, the concentration of acid impurities in the purified process stream may be less than about 10 ppm. More preferably, the concentration of acid impurities in the purified process stream may be less than about 5 ppm. Most preferably, the concentration of acid impurities in the purified process stream may be less than about 1 ppm.

The concentration of water in the purified process stream after reacting with a basic aqueous solution and/or contacting with an acid active agent to remove at least some acid impurities, drying the process stream to remove at least some water, and separating at least some of the organic impurities from the process stream may be less than about 100 parts per million (ppm). Preferably, the concentration of water in the purified process stream may be less than about 50 ppm. More preferably, the concentration of water in the purified process stream may be less than about 30 ppm. Most preferably, the concentration of water in the purified process stream may be less than about 10 ppm.

It has been found that the purified process stream produced as described above may result in a high-purity $CF_3I$ product. The process produces good process yields and is amenable for the manufacture of $CF_3I$ on a commercial scale.

FIG. 1 is a process flow diagram showing a process 10 for manufacturing high-purity $CF_3I$. As shown in FIG. 1, the process 10 may comprise a crude process stream 12 and a basic aqueous solution 14 flowing into a scrubber 16. The crude process stream 12 and the basic aqueous solution 14 may be as described above. The basic aqueous solution 14 may react with the crude process stream 12 within the scrubber 16 to neutralize and dissolve acid impurities found in the crude process stream 12 to form a first intermediate process stream 18. The reacted basic aqueous solution 14 with the neutralized and dissolved acid impurities may flow out of the scrubber through a scrubber waste stream 20 for disposal or recycle.

The first intermediate process stream 18 may flow to an adsorption column 22. The adsorption column 22 may contain any of the desiccants described above. As the first intermediate process stream 18 contacts the desiccant within the adsorption column 22, the desiccant adsorbs water in the first intermediate process stream 18 to produce a dried, second intermediate process stream 24.

The second intermediate process stream 24 may flow to a first distillation column 26. The first distillation column 26 may be configured to separate organic impurities having a lower boiling point than $CF_3I$ from the second intermediate process stream 24. The separated organic impurities having a lower boiling point than $CF_3I$ may be removed through a volatile organic overhead stream 30. The $CF_3I$ and remaining organic impurities may flow out of the bottom of the first distillation column 26 to form a third intermediate process stream 32.

The third intermediate process stream 32 may flow to a second distillation column 34. The second distillation column 34 may be configured to separate organic impurities having a higher boiling point than $CF_3I$ from the third intermediate process stream 32. The high-purity $CF_3I$ is collected from a product overhead process stream 36, as described above. The organic impurities having a higher boiling point than $CF_3I$, such as $CH_3I$, may flow out of the bottom of the second distillation column 34 to form a non-volatile organic waste stream 38.

Figure 2:
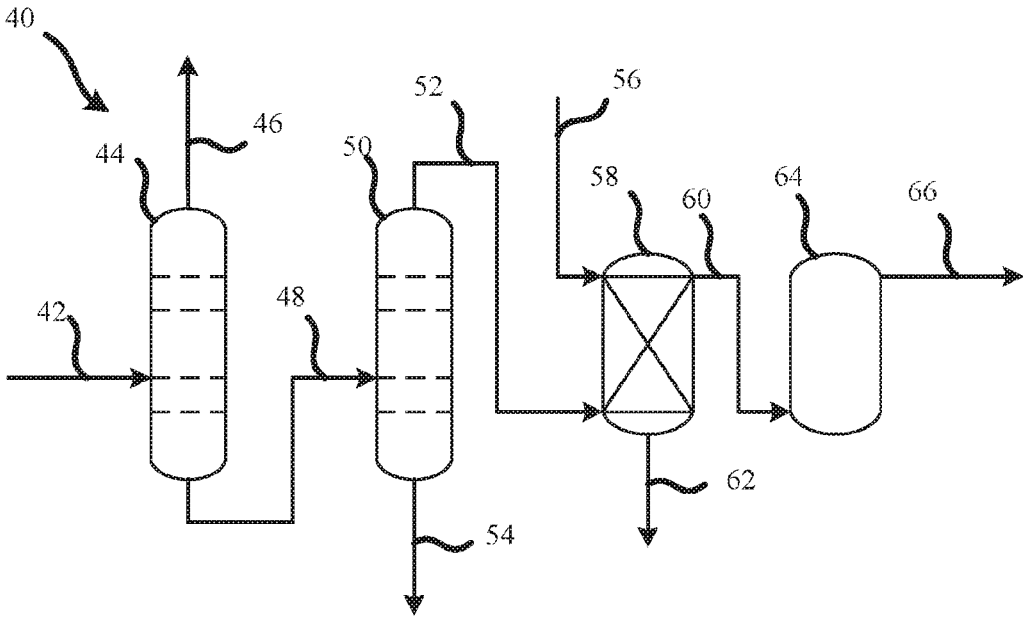
FIG. 2 is a process flow diagram showing another process for producing high-purity trifluoroiodomethane.

FIG. 2 is a process flow diagram showing another process 40 for manufacturing high-purity $CF_3I$. As shown in FIG. 2, the process 40 may comprise a crude process stream 42 flowing into to a first distillation column 44. The crude process stream 42 may be as described above. The first distillation column 44 may be configured to separate organic impurities having a lower boiling point than $CF_3I$ from the crude process stream 42. The separated organic impurities having a lower boiling point than $CF_3I$ may be removed through a volatile organic overhead stream 46. The $CF_3I$ and remaining organic impurities may flow out of the bottom of the first distillation column 44 to form a first intermediate process stream 48.

The first intermediate process stream 48 may flow to a second distillation column 50. The second distillation column 50 may be configured to separate organic impurities having a higher boiling point than $CF_3I$ from the first intermediate process stream 48 to form a second intermediate process stream 52 from the overhead of the second distillation column 50. The organic impurities having a higher boiling point than $CF_3I$, such as $CH_3I$, may flow out of the bottom of the second distillation column 50 to form a non-volatile organic waste stream 54.

The second intermediate process stream 52 and a basic aqueous solution 56 may flow into a scrubber 58. The basic aqueous solution may be as described above. The basic aqueous solution 56 may react with the second intermediate process stream 52 within the scrubber 58 to neutralize and dissolve acid impurities found in the second intermediate process stream 52 to form a third intermediate process stream 60. The reacted basic aqueous solution 56 with the neutralized and dissolved acid impurities may flow out of the scrubber through a scrubber waste stream 62 for disposal or recycle.

The third intermediate process stream 60 may flow to an adsorption column 64. The adsorption column 64 may contain any of the desiccants described above. As the third intermediate process stream 60 contacts the desiccant within the adsorption column 64, the desiccant adsorbs water in the third intermediate process stream 60 to produce a dried, high-purity $CF_3I$ process stream 66, as described above.

Figure 3:
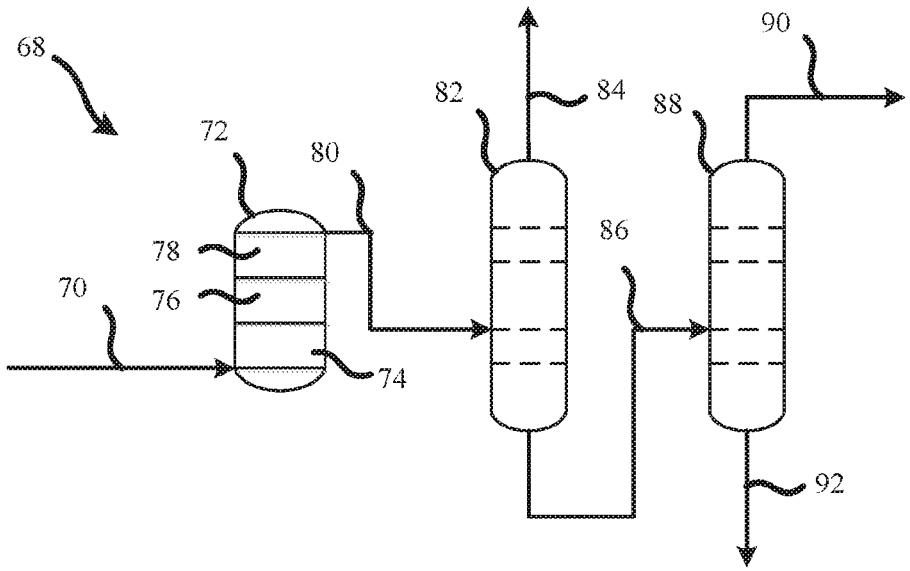
FIG. 3 is a process flow diagram showing another process for producing high-purity trifluoroiodomethane.

FIG. 3 is a process flow diagram showing another process 68 for manufacturing high-purity $CF_3I$. As shown in FIG. 3, the process 68 may comprise a crude process stream 70 an adsorption column 72. The crude process stream 70 may be as described above. The adsorption column 72 may include a first acid active agent 74, a second acid active agent 76, and a desiccant 78. The first acid active agent 74 may be any of the acid active agents described above, such as alumina P-188, for example. The second acid active agent 76 may be any of the acid active agents described above, so long as it is different from the first acid active agent 74. The second acid active agent 76 may be alumina CLR-204, for example. The use of more than one acid active agent may be preferred, as different acid active agents may have a greater affinity for different acid impurities. The desiccant 78 may be any of the desiccants describe above, such as a 3 A molecular sieve, for example.

The crude process stream 70 may flow into the adsorption column 72 and contact the first acid active agent 74, and then contact the second acid active agent 76 to remove at least some of the acid impurities from the crude process stream 70. The crude process stream 70 may then contact the desiccant 78 to remove at least some of the water from the crude process stream 70 to produce a first intermediate process stream 80.

The first intermediate process stream 80 may flow to a first distillation column 82. The first distillation column 82 may be configured to separate organic impurities having a lower boiling point than $CF_3I$ from the first intermediate process stream 80. The separated organic impurities having a lower boiling point than $CF_3I$ may be removed through a volatile organic overhead stream 84. The $CF_3I$ and remaining organic impurities may flow out of the bottom of the first distillation column 82 to form a second intermediate process stream 86.

The second intermediate process stream 86 may flow to a second distillation column 88. The second distillation column 88 may be configured to separate organic impurities having a higher boiling point than $CF_3I$ from the second intermediate process stream 86. The high-purity $CF_3I$ is collected from a product overhead process stream 90, as described above. The organic impurities having a higher boiling point than $CF_3I$, such as $CH_3I$, may flow out of the bottom of the second distillation column 88 to form a non-volatile organic waste stream 92.

Figure 4:
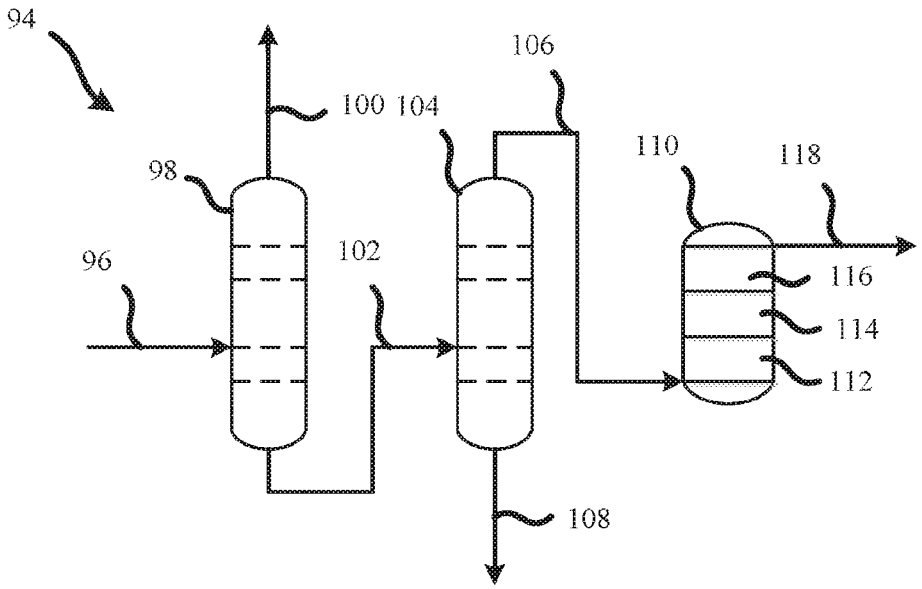
FIG. 4 is a process flow diagram showing another process for producing high-purity trifluoroiodomethane.

FIG. 4 is a process flow diagram showing another process 94 for manufacturing high-purity $CF_3I$. As shown in FIG. 4, the process 94 may comprise a crude process stream 96 flowing into to a first distillation column 98. The crude process stream 96 may be as described above. The first distillation column 98 may be configured to separate organic impurities having a lower boiling point than $CF_3I$ from the crude process stream 96. The separated organic impurities having a lower boiling point than $CF_3I$ may be removed through a volatile organic overhead stream 100. The $CF_3I$ and remaining organic impurities may flow out of the bottom of the first distillation column 98 to form a first intermediate process stream 102.

The first intermediate process stream 102 may flow to a second distillation column 104. The second distillation column 104 may be configured to separate organic impurities having a higher boiling point than $CF_3I$ from the first intermediate process stream 102 to form a second intermediate process stream 106 from the overhead of the second distillation column 104. The organic impurities having a higher boiling point than $CF_3I$, such as $CH_3I$, may flow out of the bottom of the second distillation column 104 to form a non-volatile organic waste stream 108.

The second intermediate process stream 106 may flow into an adsorption column 110. The adsorption column 110 may include a first acid active agent 112, a second acid active agent 114, and a desiccant 116. The first acid active agent 112 may be any of the acid active agents described above, such as alumina P-188, for example. The second acid active agent 114 may be any of the acid active agents described above, so long as it is different from the first acid active agent 112. The second acid active agent 114 may be alumina CLR-204, for example. The desiccant 116 may be any of the desiccants describe above, such as a 3 A molecular sieve, for example.

As the second intermediate process stream 106 flows into the adsorption column 110 and contacts the first acid active agent 112 and then contacts the second acid active agent 114, at least some of the acid impurities are removed from the second intermediate process stream 106. The second intermediate process stream 106 may then contact the desiccant 116 to remove at least some of the water from the second intermediate process stream 106 to produce a dried, high-purity $CF_3I$ process stream 118, as described above.

While this invention has been described as relative to exemplary designs, the present invention may be further modified within the spirit and scope of this disclosure. Further, this application is intended to cover such departures from the present disclosure as come within known or customary practice in the art to which this invention pertains.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

EXAMPLES

Example 1: Effect of Alkali Metal Hydroxide Concentration on Crude $CF_3I$

In this Example, the effect of alkali metal hydroxide concentration on crude $CF_3I$ according to Equations 1 and 2 described above is demonstrated. Crude starting material consisting of 99.88 GC area % $CF_3I$, 0.08 GC area % $CH_3I$, and 0.04 GC area % other organic impurities was charged in 100 g amounts into each of six, 150 ml cylinders at room temperature. The six cylinders were evacuated prior to charging with the crude starting material. Six different test solutions were prepared with concentrations of the potassium hydroxide varying from 0 wt. % to 20 wt. %. A different one of each of the six test solutions was added to each of the six cylinders in an amount of 50 ml. The average pressure in the sample cylinders was 70 psig at room temperature. The six cylinders were shaken at room temperature for five days. Five days is much longer than a typical process contact time, but was selected to provide a clearer indication of the relative effect of the various potassium hydroxide concentrations on the crude starting material.

After five days, a sample of the aqueous layer and a sample of the organic layer were withdrawn from each of the six cylinders. The six aqueous layer samples were analyzed by ion chromatography to determine the amounts of fluoride generated during the interaction between the crude $CF_3I$ and the six test solutions. The results are shown in Table 1 below. The six organic layer samples were analyzed by GC to determine changes in the concentrations of $CF_3I$, $CH_3I$, and the other organic impurities. The results are shown in Table 2.

Table 1 lists the fluoride concentrations in ppm normalized to the amount of $CF_3I$ crude for each of the six potassium hydroxide concentrations. The control sample shows the total free fluoride in the crude $CF_3I$. Normalization was done for each sample by dividing the fluoride concentration as measured by ion chromatography by the total mass of $CF_3I$ in the crude sample as measured by GC.

TABLE 1

| KOH Concentration (wt. %) | Fluoride Concentration (ppm) |
|---|---|
| 0 (Control) | 0.2 |
| 0.5 | 10.5 |
| 1 | 16.7 |
| 5 | 18 |
| 10 | 54.7 |
| 20 | 78.3 |

As shown in Table 1, at potassium hydroxide concentrations above about 0.5 wt. %, the fluoride concentration increased by more than 10 ppm over the control sample which was not exposed to potassium hydroxide. It is believed that the increase in fluoride is due entirely to the breakdown of $CF_3I$. Thus, to maintain a high $CF_3I$ yield through the purification process, it may be preferred that the potassium hydroxide concentration be from about 0.01 wt. % to about 0.5 wt. %.

Table 2 lists the concentrations of $CF_3I$, $CH_3I$, and the other organic impurities for each of the six potassium hydroxide concentrations.

TABLE 2

| KOH Concentration | GC Analysis of Organic Phase (as GC area %) | | | |
|---|---|---|---|---|
| (wt. %) | CF3I | CH3I | Change | Others |
| 0 | 99.8855 | 0.0824 | 0% | 0.0321 |
| 0.5 | 99.8936 | 0.0810 | −2% | 0.0254 |

TABLE 2-continued

| KOH Concentration | GC Analysis of Organic Phase (as GC area %) | | | |
|---|---|---|---|---|
| (wt. %) | CF3I | CH3I | Change | Others |
| 1 | 99.8989 | 0.0781 | −5% | 0.023 |
| 5 | 99.9115 | 0.0582 | −29% | 0.0303 |
| 10 | 99.9268 | 0.0418 | −49% | 0.0314 |
| 20 | 99.9395 | 0.0268 | −67% | 0.0337 |

As shown in Table 2, at potassium hydroxide concentrations above about 1 wt. %, a significant portion of the $CH_3I$ present in the crude $CF_3I$ is removed by the potassium hydroxide solution. Thus, to remove significant amounts of $CH_3I$, it may be preferred that the potassium hydroxide concentration be from about 1 wt. % to about 20 wt. %. Considering Tables 1 and 2 together, when balancing preservation of $CF_3I$ and removal of $CH_3I$, it may be preferred that the potassium hydroxide concentration be from about 0.5 wt. % to about 5 wt. %.

Example 2: Effect of Alkali Metal Carbonate Concentration on Crude $CF_3I$

In this Example, the effect of alkali metal carbonate concentration on crude $CF_3I$ according to Equations 1 and 2 described above is demonstrated. Crude starting material consisting of 99.88 GC area % $CF_3I$, 0.08 GC area % $CH_3I$, and 0.03 GC area % other organic impurities was charged in 100 g amounts into each of six, 150 ml cylinders at room temperature. The six cylinders were evacuated prior to charging with the crude starting material. Six different test solutions were prepared with concentrations of the sodium carbonate varying from 0 wt. % to 20 wt. %. A different one of each of the six test solutions was added each of the six cylinders in an amount of 50 ml. The average pressure in the sample cylinders was 70 psig at room temperature. The six cylinders were shaken at room temperature for five days. Five days is much longer than a typical process contact time, but was selected to provide a clearer indication of the relative effect of the various sodium carbonate concentrations on the crude starting material.

After five days, a sample of the aqueous layer and a sample of the organic layer were withdrawn from each of the six cylinders. The six aqueous layer samples were analyzed by ion chromatography to determine the amounts of fluoride generated during the interaction between the crude $CF_3I$ and the six test solutions. The results are shown in Table 3 below.

Table 3 lists the fluoride concentrations in ppm normalized to the amount of $CF_3I$ crude for each of the six sodium carbonate concentrations.

TABLE 3

| $Na_2CO_3$ Concentration (wt. %) | Fluoride Concentration (ppm) |
|---|---|
| 0 (Control) | 0.2 |
| 0.5 | 0.4 |
| 1 | 2 |
| 5 | 5.2 |
| 10 | 46.4 |
| 20 | 59.6 |

As shown in Table 3, at sodium carbonate concentrations above between about 5 wt. % and 10 wt. %, the fluoride concentration increased by more than 10 ppm over the control sample which was not exposed to sodium carbonate.

It is believed that the increase in fluoride is due entirely to the breakdown of $CF_3I$. Thus, to maintain a high $CF_3I$ yield through the purification process, it may be preferred that the sodium carbonate concentration be from about 0.5 wt. % to about 5 wt.

The six organic layer samples were analyzed by GC to determine changes in the concentrations of $CF_3I$, $CH_3I$, and the other organic impurities. No significant differences were observed between the six organic layer samples. Thus, the sodium carbonate solutions had no significant impact on $CH_3I$ concentrations even at concentrations up to 20 wt. %. Without wishing to be bound by any theory, it is believed that the difference in reactivity between the potassium hydroxide and sodium carbonate with respect to removal of $CH_3I$ may be attributed to the fact that the hydroxide ion is a better nucleophile than the carbonate ion and readily undergoes substitution reactions with $CH_3I$. This same effect may also explain why the potassium hydroxide is observed to break down the $CF_3I$ at lower concentrations than the sodium carbonate.

Example 3: Acid Impurity and Water Removal from Crude $CF_3I$ Using Alumina

In this Example, the effectiveness of alumina in removing acid impurities from crude $CF_3I$ is demonstrated. An adsorption column made of 24-inch long, three quarter inch diameter, perfluoroalkoxy alkane polymer tube was prepared by including a layer of P-188 alumina, a layer of CLR-204 alumina, and a layer of 3 A molecular sieve. Each layer was about eight inches long. An additional thin layer of indicating anhydrous calcium sulfate was inserted in the 3 A molecular sieve layer to indicate when the 3 A molecular layer was spent. The column was wrapped in foil to prevent interaction with light.

About 30 lbs. of crude $CF_3I$ was circulated through the column in a liquid phase. The crude $CF_3I$ entered the column through the two alumina layers and exited through the 3 A molecular sieve layer. The crude $CF_3I$ circulated through the column for seven days. Seven days is much longer than a typical process contact time, but was selected to provide a clearer indication of the relative effect of the two alumina layers on the crude starting material.

After seven days, samples of the crude $CF_3I$ were analyzed for acid impurity concentration and water concentration. The acid impurity concentration was measured by acid-base titration. The water concentration was measured by Karl-Fisher titration. The results are shown in Table 4 below.

TABLE 4

| Material | Acidity as HCl (ppm) | Water (ppm) |
|---|---|---|
| Crude $CF_3I$ Initially | 91.2 | 15.6 |
| Crude $CF_3I$ After 7 Days | 6.5 | 1.8 |

Samples of the crude $CF_3I$ were also analyzed by GC to determine changes in the concentrations of $CF_3I$, $CH_3I$, and the other organic impurities. The results are shown in Table 5.

TABLE 5

| | GC Analysis of Organic Phase (as GC area %) | | |
|---|---|---|---|
| Material | CF3I | CH3I | Other |
| Crude CF3I Initially | 99.4302 | 0.3133 | 0.2565 |
| Crude CF3I After 7 Days | 99.4962 | 0.2981 | 0.2057 |

Considering Tables 4 and 5 together, the adsorption column including alumina and desiccant significantly reduced the acid impurities and water, while causing no measurable breakdown of $CF_3I$.

Example 4: Distillation of Crude $CF_3I$

In this Example, the effectiveness of distillation in removing $CH_3I$ from crude $CF_3I$ is demonstrated. To the reboiler of a distillation column was charged 180 lbs. of crude starting material consisting of 99.4 GC area % $CF_3I$, 0.4 GC area % $CH_3I$, and 0.2 GC area % other organic impurities. The distillation column was operated at a pressure ranging from 60 to 80 psig, a temperature ranging from 30 to 40° C., and a differential pressure of from 10 to 30 inches of water. The take-off rate ranged from 0.5 to 3 lbs./hour.

About 5 to 10 lbs. of non-condensable gases and low-boiling point impurities were removed through the overhead stream, followed by $CF_3I$. The purity of the $CF_3I$ was greater than 99.99% with a level of $CH_3I$ below 5 ppm. The yield of the distillation ranged from 90 to 97%. $CH_3I$ and other high-boiling point impurities concentrated in the reboiler. After distillation, about 2-5 lbs. of organic impurities were collected from the reboiler.

Example 5: Purification Process for Crude $CF_3I$

In this Example, the effectiveness of a purification process is demonstrated. Crude feed material in the amount of 11,323 lbs. was bubbled through 1,382 lbs. of an aqueous 0.52 wt. % KOH solution. The crude feed material consisted of $CF_3I$ (99.78 GC area %), $CH_3I$ (0.15 GC area %), and others (0.07 GC area %), with total acidity of 50 ppm, and moisture content of 15 ppm. A source tank containing the crude feed material was maintained at a temperature of about 30° C. as the crude feed material was charged, at a flow rate of about 5 lbs./min, into a caustic tank containing the 0.5 wt. % KOH solution, by means of a differential pressure. The crude feed material was bubbled through the 0.5 wt. % KOH solution as a gas. Assuming that at any instance the crude feed material (gas) contacts only about 10% of the 0.5 wt. % KOH solution in the tank, the flow rate of about 5 lbs./min corresponds to a contact time of about 27.64 min. A resulting effluent gas stream from the caustic tank was passed through a drying column charged with 3 A molecular sieves, and then consolidated in the reboiler of a distillation column.

During distillation in the distillation column, chilled water at between about 2° C. and 5° C. was circulated through the condenser at the top of the distillation column, while the temperature of the reboiler was maintained between about 10° C. and 20° C. During the distillation, 283 lbs. of non-condensable gases and low-boiling point impurities were removed through the overhead stream, followed by 10,312 lbs. of $CF_3I$, at a rate of about 250 lbs./h. The $CF_3I$ obtained was measured by GC and found to have a purity greater than 99.99 wt. %, with a $CH_3I$ concentration less than 5 ppm, a total acid concentration of less than 0.1 ppm, and a moisture concentration of less than 5 ppm. About 390 lbs. of higher-boiling impurities were recovered from the reboiler. The material balance for the integrated purification process was about 97% and the yield was about 91%. Ion chromatography analysis of the 0.5 wt. % KOH solution after the contacting the crude feed material revealed presence of about 10 ppm of fluoride ions. This indicates that despite the long contact time, insignificant amounts of $CF_3I$ reacted with the KOH during the acid removal step in the caustic tank containing the 0.5 wt. % KOH solution.

ASPECTS

Aspect 1 is a method for purifying trifluoroiodomethane, the method comprising providing a process stream comprising trifluoroiodomethane, organic impurities, and acid impurities, reacting the process stream with a basic aqueous solution, the basic aqueous solution comprising water and at least one base selected from the group of an alkali metal carbonate and an alkali metal hydroxide, and separating at least some of the organic impurities from the process stream.

Aspect 2 is the method of Aspect 1, wherein the basic aqueous solution consists essentially of water and the at least one base selected from the group of an alkali metal carbonate and an alkali metal hydroxide.

Aspect 3 is the method of Aspect 2, wherein the basic aqueous solution consists of water and the at least one base selected from the group of an alkali metal carbonate and an alkali metal hydroxide.

Aspect 4 is the method of any of Aspects 1-3, wherein in the reacting step, the base comprises an alkali metal carbonate.

Aspect 5 is the method of Aspect 4, wherein in the reacting step, the base consists essentially of an alkali metal carbonate.

Aspect 6 is the method of Aspect 4, wherein in the reacting step, the base consists of an alkali metal carbonate.

Aspect 7 is the method of any of Aspects 4-6, wherein a concentration of the alkali metal carbonate in the basic aqueous solution is from about 0.01 wt. % to about 20 wt. %.

Aspect 8 is the method of any of Aspects 4-6, wherein a concentration of the alkali metal carbonate in the basic aqueous solution is from about 0.1 wt. % to about 10 wt. %.

Aspect 9 is the method of any of Aspects 4-6, wherein a concentration of the alkali metal carbonate in the basic aqueous solution is from about 0.5 wt. % to about 5 wt. %.

Aspect 10 is the method of any of Aspects 4-6, wherein a concentration of the alkali metal carbonate in the basic aqueous solution is about 5 wt. %.

Aspect 11 is the method of any of Aspects 4-10, wherein the alkali metal carbonate is selected from the group consisting of sodium carbonate, potassium carbonate, lithium carbonate, and combinations thereof.

Aspect 12 is the method of Aspect 11, wherein the alkali metal carbonate comprises sodium carbonate.

Aspect 13 is the method of either of Aspects 11 or 12, wherein the alkali metal carbonate comprises potassium carbonate.

Aspect 14 is the method of any of Aspects 11-13, wherein the alkali metal carbonate comprises lithium carbonate.

Aspect 15 is the method of Aspect 11, wherein the alkali metal carbonate consists essentially of sodium carbonate.

Aspect 16 is the method of Aspect 11, wherein the alkali metal carbonate consists of sodium carbonate.

Aspect 17 is the method of Aspect 11, wherein the alkali metal carbonate consists essentially of potassium carbonate.

Aspect 18 is the method of Aspect 11, wherein the alkali metal carbonate consists of potassium carbonate.

Aspect 19 is the method of Aspect 11, wherein the alkali metal carbonate consists essentially of lithium carbonate.

Aspect 20 is the method of Aspect 11, wherein the alkali metal carbonate consists of lithium carbonate.

Aspect 21 is the method of any of Aspects 1-3, wherein in the reacting step, the base comprises an alkali metal hydroxide.

Aspect 22 is the method of Aspect 21, wherein in the reacting step, the base consists essentially of an alkali metal hydroxide.

Aspect 23 is the method of Aspect 21, wherein in the reacting step, the base consists of an alkali metal hydroxide.

Aspect 24 is the method of any of Aspects 21-23, wherein a concentration of the alkali metal hydroxide in the basic aqueous solution is from about 0.01 wt. % to about 20 wt. %.

Aspect 25 is the method of any of Aspects 21-23, wherein a concentration of the alkali metal hydroxide in the basic aqueous solution is from about 0.1 wt. % to about 5 wt. %.

Aspect 26 is the method of any of Aspects 21-23, wherein a concentration of the alkali metal hydroxide in the basic aqueous solution is from about 0.5 wt. % to about 1 wt. %.

Aspect 27 is the method of any of Aspects 21-23, wherein a concentration of the alkali metal hydroxide in the basic aqueous solution is about 0.5 wt. %.

Aspect 28 is the method of any of Aspects 21-27, wherein the alkali metal hydroxide is selected from the group consisting of sodium hydroxide, potassium hydroxide, lithium hydroxide, and combinations thereof.

Aspect 29 is the method of Aspect 28, wherein the alkali metal hydroxide comprises sodium hydroxide.

Aspect 30 is the method of either of Aspects 28 or 29, wherein the alkali metal hydroxide comprises potassium hydroxide.

Aspect 31 is the method of any of Aspects 28-30, wherein the alkali metal hydroxide comprises lithium hydroxide.

Aspect 32 is the method of Aspect 28, wherein the alkali metal hydroxide consists essentially of sodium hydroxide.

Aspect 33 is the method of Aspect 28, wherein the alkali metal hydroxide consists of sodium hydroxide.

Aspect 34 is the method of Aspect 28, wherein the alkali metal hydroxide consists essentially of potassium hydroxide.

Aspect 35 is the method of Aspect 28, wherein the alkali metal hydroxide consists of potassium hydroxide.

Aspect 36 is the method of Aspect 28, wherein the alkali metal hydroxide consists essentially of lithium hydroxide.

Aspect 37 is the method of Aspect 28, wherein the alkali metal hydroxide consists of lithium hydroxide.

Aspect 38 is the method of any of Aspects 1-37, wherein in the reacting step, a temperature of the process stream is from about 5° C. to about 80° C.

Aspect 39 is the method of any of Aspects 1-37, wherein in the reacting step, a temperature of the process stream is from about 10° C. to about 50° C.

Aspect 40 is the method of any of Aspects 1-37, wherein in the reacting step, a temperature of the process stream is from about 20° C. to about 40° C.

Aspect 41 is the method of any of Aspects 1-40, wherein in the reacting step, a pressure of the process stream is from about 1 psig to about 100 psig.

Aspect 42 is the method of any of Aspects 1-40, wherein in the reacting step, a pressure of the process stream is from about 3 psig to about 80 psig.

Aspect 43 is the method of any of Aspects 1-40, wherein in the reacting step, a pressure of the process stream is from about 5 psig to about 50 psig.

Aspect 44 is the method of any of Aspects 1-43, wherein the method is a continuous process.

Aspect 45 is the method of any of Aspects 1-43, wherein the method is a batch process.

Aspect 46 is the method of any of Aspects 1-45, wherein in the providing step, the organic impurities include methyl iodide, and the base comprises an alkali metal hydroxide, a concentration of the methyl iodide in the process stream, in GC area % of total organic compounds, is reduced by about 1% to about 70% by the reacting step.

Aspect 47 is the method of any of Aspects 1-45, wherein in the providing step, the organic impurities include methyl iodide, and the base comprise an alkali metal hydroxide, a concentration of the methyl iodide in the process stream, in GC area % of total organic compounds, is reduced by about 5% to about 50% by the reacting step.

Aspect 48 is the method of any of Aspects 1-45, wherein in the providing step, the organic impurities include methyl iodide, and the base comprises an alkali metal hydroxide, a concentration of the methyl iodide in the process stream, in GC area % of total organic compounds, is reduced by about 5% to about 30% by the reacting step.

Aspect 49 is method of any of Aspects 1-46, wherein the reacting step precedes the separation step.

Aspect 50 is the method of any of Aspects 1-46, wherein the reacting step follows the separation step.

Aspect 51 is the method of any of Aspects 1-48, further comprising the additional step of drying to remove at least some of the water from the process stream immediately after the reacting step.

Aspect 52 is the method of Aspect 51, wherein the drying step comprises contacting the process stream with a desiccant.

Aspect 53 is the method of Aspect 52, wherein the desiccant comprises at least one adsorbent selected from the group of anhydrous calcium chloride, anhydrous calcium sulfate, concentrated sulfuric acid, silica, activated charcoal and zeolites.

Aspect 54 is the method of Aspect 51, wherein the drying step comprises passing the process stream through at least one 3 A molecular sieve.

Aspect 55 is the method of any of Aspects 1-54, wherein after the reacting step, the drying step, and the separation step, the process stream includes at least about 99 wt. % trifluoroiodomethane.

Aspect 56 is the method of any of Aspects 1-54, wherein after the reacting step, the drying step, and the separation step, the process stream includes at least about 99.5 wt. % trifluoroiodomethane.

Aspect 57 is the method of any of Aspects 1-54, wherein after the reacting step, the drying step, and the separation step, the process stream includes at least about 99.9 wt. % trifluoroiodomethane.

Aspect 58 is the method of any of Aspects 1-52, wherein after the reacting step, the drying step, and the separation step, the process stream includes at least about 99.99 wt. % trifluoroiodomethane.

Aspect 59 is the method of any of Aspects 1-58, wherein after the reacting step, the drying step, and the separation step, the process stream includes less than about 50 ppm methyl iodide.

Aspect 60 is the method of any of Aspects 1-58, wherein after the reacting step, the drying step, and the separation step, the process stream includes less than about 20 ppm methyl iodide.

Aspect 61 is the method of any of Aspects 1-58, wherein after the reacting step, the drying step, and the separation step, the process stream includes less than about 10 ppm methyl iodide.

Aspect 62 is the method of any of Aspects 1-58, wherein after the reacting step, the drying step, and the separation step, the process stream includes less than about 5 ppm methyl iodide.

Aspect 63 is the method of any of Aspects 1-62, wherein after the reacting step, the drying step, and the separation step, the process stream includes less than about 20 ppm acid impurities.

Aspect 64 is the method of any of Aspects 1-62, wherein after the reacting step, the drying step, and the separation step, the process stream includes less than about 10 ppm acid impurities.

Aspect 65 is the method of any of Aspects 1-62, wherein after the reacting step, the drying step, and the separation step, the process stream includes less than about 5 ppm acid impurities.

Aspect 66 is the method of any of Aspects 1-62, wherein after the reacting step, the drying step, and the separation step, the process stream includes less than about 1 ppm acid impurities.

Aspect 67 is the method of any of Aspects 1-66, wherein after the reacting step, the drying step, and the separation step, the process stream includes less than about 100 ppm water.

Aspect 68 is the method of any of Aspects 1-66, wherein after the reacting step, the drying step, and the separation step, the process stream includes less than about 50 ppm water.

Aspect 69 is the method of any of Aspects 1-66, wherein after the reacting step, the drying step, and the separation step, the process stream includes less than about 30 ppm water.

Aspect 70 is the method of any of Aspects 1-66, wherein after the reacting step, the drying step, and the separation step, the process stream includes less than about 10 ppm water.

Aspect 71 is the method of any of Aspects 1-70, wherein the separating step comprises distilling the process stream.

Aspect 72 is the method of Aspect 71, wherein in distilling the process stream comprises a first distillation to remove from the process stream organic impurities having a lower boiling point than $CF_3I$, and a second distillation to remove from the process stream organic impurities having a higher boiling point than $CF_3I$.

Aspect 73 is the method of Aspect 71, wherein distilling the process stream comprises removing organic impurities having a lower boiling point than $CF_3I$ through an overhead stream, followed by obtaining $CF_3I$ through the overhead stream while organic impurities having a higher boiling point than $CF_3I$ concentrate in a reboiler.

Aspect 74 is a method for purifying trifluoroiodomethane, the method comprising providing a process stream comprising trifluoroiodomethane, organic impurities, and acid impurities, contacting the process stream with an acid reactive agent, and separating at least some of the organic impurities from the process stream.

Aspect 75 is the method of Aspect 74, wherein the acid reactive agent comprises at least one adsorbent selected from the group of alumina, alkali metal oxides, alkaline earth metal oxides, metal hydroxides, aluminosilicate minerals, zirconias, and silica.

Aspect 76 is the method of Aspect 74, wherein the acid reactive agent comprises alumina.

Aspect 77 is the method of any of Aspects 74-76, wherein in the contacting step, the process stream is in a liquid phase, and a temperature of the process stream is from about −50° C. to about 50° C.

Aspect 78 is the method of any of Aspects 74-76, wherein in the contacting step, the process stream is in a liquid phase, and a temperature of the process stream is from about 0° C. to about 35° C.

Aspect 79 is the method of any of Aspects 74-76, wherein in the contacting step, the process stream is in a liquid phase, and a temperature of the process stream is from about 10° C. to about 30° C.

Aspect 80 is the method of any of Aspects 74-79, wherein in the contacting step, the process stream is in a liquid phase, and a pressure of the process stream is from about 1 psig to about 100 psig.

Aspect 81 is the method of any of Aspects 74-79, wherein in the contacting step, the process stream is in a liquid phase, and a pressure of the process stream is from about 10 psig to about 90 psig.

Aspect 82 is the method of any of Aspects 74-79, wherein in the contacting step, the process stream is in a liquid phase, and a pressure of the process stream is from about 20 psig to about 50 psig.

Aspect 83 is the method of any of Aspects 74-76, wherein in the contacting step, the process stream is in a gas phase, and a temperature of the process stream is from about −20° C. to about 60° C.

Aspect 84 is the method of any of Aspects 74-76, wherein in the contacting step, the process stream is in a gas phase, and a temperature of the process stream is from about −5° C. to about 50° C.

Aspect 85 is the method of any of Aspects 74-76, wherein in the contacting step, the process stream is in a gas phase, and a temperature of the process stream is from about 15° C. to about 40° C.

Aspect 86 is the method of any of Aspects 74-76 and 83-85, wherein in the contacting step, the process stream is in a gas phase, and a pressure of the process stream is from about 1 psig to about 100 psig.

Aspect 87 is the method of any of Aspects 74-76 and 83-85, wherein in the contacting step, the process stream is in a gas phase, and a pressure of the process stream is from about 10 psig to about 90 psig.

Aspect 88 is the method of any of Aspects 74-76 and 83-85, wherein in the contacting step, the process stream is in a gas phase, and a pressure of the process stream is from about 15 psig to about 80 psig.

Aspect 89 is the method of any of Aspects 74-88, wherein the method is a continuous process.

Aspect 90 is the method of any of Aspects 74-88, wherein the method is a batch process.

Aspect 91 is method of any of Aspects 74-90, wherein the contacting step precedes the separation step.

Aspect 92 is the method of any of Aspects 74-90, wherein the contacting step follows the separation step.

Aspect 93 is the method of any of Aspects 74-92, further comprising the additional step of drying to remove at least some of the water from the process stream immediately after the contacting step.

Aspect 94 is the method of Aspect 93, wherein the drying step comprises bringing the process stream into contact with a desiccant.

Aspect 95 is the method of Aspect 94, wherein the desiccant comprises at least one adsorbent selected from the group of anhydrous calcium chloride, anhydrous calcium sulfate, concentrated sulfuric acid, silica, activated charcoal and zeolites.

Aspect 96 is the method of Aspect 93, wherein the drying step comprises passing the process stream through at least one 3 A molecular sieve.

Aspect 97 is the method of any of Aspects 74-96, wherein after the contacting step, the drying step, and the separation step, the process stream includes at least about 99 wt. % trifluoroiodomethane, less than about 50 ppm methyl iodide, less than about 100 ppm water, and less than about 20 ppm acid impurities.

Aspect 98 is the method of any of Aspects 74-97, wherein after the reacting step, the drying step, and the separation step, the process stream includes at least about 99 wt. % trifluoroiodomethane.

Aspect 99 is the method of any of Aspects 74-97, wherein after the reacting step, the drying step, and the separation step, the process stream includes at least about 99.5 wt. % trifluoroiodomethane.

Aspect 100 is the method of any of Aspects 74-97, wherein after the reacting step, the drying step, and the separation step, the process stream includes at least about 99.9 wt. % trifluoroiodomethane.

Aspect 101 is the method of any of Aspects 74-97, wherein after the reacting step, the drying step, and the separation step, the process stream includes at least about 99.99 wt. % trifluoroiodomethane.

Aspect 102 is the method of any of Aspects 74-101, wherein after the reacting step, the drying step, and the separation step, the process stream includes less than about 50 ppm methyl iodide.

Aspect 103 is the method of any of Aspects 74-101, wherein after the reacting step, the drying step, and the separation step, the process stream includes less than about 20 ppm methyl iodide.

Aspect 104 is the method of any of Aspects 74-101, wherein after the reacting step, the drying step, and the separation step, the process stream includes less than about 10 ppm methyl iodide.

Aspect 105 is the method of any of Aspects 74-101, wherein after the reacting step, the drying step, and the separation step, the process stream includes less than about 5 ppm methyl iodide.

Aspect 106 is the method of any of Aspects 74-105, wherein after the reacting step, the drying step, and the separation step, the process stream includes less than about 20 ppm acid impurities.

Aspect 107 is the method of any of Aspects 74-105, wherein after the reacting step, the drying step, and the separation step, the process stream includes less than about 10 ppm acid impurities.

Aspect 108 is the method of any of Aspects 74-105, wherein after the reacting step, the drying step, and the separation step, the process stream includes less than about 5 ppm acid impurities.

Aspect 109 is the method of any of Aspects 74-105, wherein after the reacting step, the drying step, and the separation step, the process stream includes less than about 1 ppm acid impurities.

Aspect 110 is the method of any of Aspects 74-109, wherein after the reacting step, the drying step, and the separation step, the process stream includes less than about 100 ppm water.

Aspect 111 is the method of any of Aspects 74-109, wherein after the reacting step, the drying step, and the separation step, the process stream includes less than about 50 ppm water.

Aspect 112 is the method of any of Aspects 74-109, wherein after the reacting step, the drying step, and the separation step, the process stream includes less than about 30 ppm water.

Aspect 113 is the method of any of Aspects 74-109, wherein after the reacting step, the drying step, and the separation step, the process stream includes less than about 10 ppm water.

Aspect 114 is the method of any of Aspects 74-113, wherein the separating step comprises distilling the process stream.

Aspect 115 is the method of Aspect 114, wherein in distilling the process stream comprises a first distillation to remove from the process stream organic impurities having a lower boiling point than $CF_3I$, and a second distillation to remove from the process stream organic impurities having a higher boiling point than $CF_3I$.

Aspect 115 is the method of Aspect 114, wherein distilling the process stream comprises removing organic impurities having a lower boiling point than $CF_3I$ through an overhead stream, followed by $CF_3I$ through the overhead stream while organic impurities having a higher boiling point than $CF_3I$ concentrate in a reboiler.

What is claimed is:

1. A method for purifying trifluoroiodomethane, the method comprising:

providing a process stream comprising trifluoroiodomethane, organic impurities, and acid impurities;

reacting the process stream with a basic aqueous solution, the basic aqueous solution comprising water and an alkali metal carbonate, wherein a concentration of the alkali metal carbonate in the basic aqueous solution is from about 0.5 wt. % to about 5 wt. %; and separating at least some of the organic impurities from the process stream.

2. The method of claim 1, wherein the alkali metal carbonate comprises sodium carbonate.

3. The method of claim 1, wherein in the reacting step, a temperature of the process stream is from about 5° C. to about 80° C. and a pressure of the process stream is from about 1 psig to about 100 psig.

4. The method of claim 1, wherein in the providing step, the organic impurities include methyl iodide, and a concentration of the methyl iodide in the process stream, in GC [area %] *area*% of total organic compounds, is reduced by from about 1% to about 70% by the reacting step.

5. The method of claim 1, further comprising an additional step of drying to remove at least some of the water from the process stream immediately after the reacting step.

6. The method of claim 5, wherein after the reacting step, the drying step, and the separation step, the process stream includes at least about 99 wt. % trifluoroiodomethane, less than about 50 ppm methyl iodide, less than about 100 ppm water, and less than about 20 ppm acid impurities.

7. A method for purifying trifluoroiodomethane, the method comprising:

providing a [process] stream comprising trifluoroiodomethane, organic impurities, and acid impurities;

contacting the [process] stream *in the liquid phase* with an acid [reactive] *active* agent *comprising an adsorbent*; and separating at least some of the organic impurities from the process stream.

8. The method of claim 7, wherein the acid [reactive] *active* agent comprises an alumina adsorbent.

9. The method of claim 7, wherein [in the contacting step, the process stream is in a liquid phase,] a temperature of the [process] stream is from about −50° C. to about 50° C. and a pressure of the [process] stream is from about 1 psig to about 100 psig.

10. The method of claim 7, wherein [in the contacting step, the process stream is in a gas phase,] a temperature of the [process] stream is from about −20° C. to about 60° C. and a pressure of the process stream is from about 1 psig to about 100 psig.

11. The method of claim 7, wherein the contacting step precedes the separation step.

12. The method of claim 7, further comprising an additional step of drying to remove at least some of the water from the [process] stream immediately after the contacting step.

13. The method of claim 12, wherein after the contacting step, the drying step, and the separation step, the [process] stream includes at least about 99 wt. % trifluoroiodomethane, less than about 50 ppm methyl iodide, less than about 100 ppm water, and less than about 20 ppm acid impurities.

14. A method for purifying trifluoroiodomethane, the method comprising:

providing a process stream comprising trifluoroiodomethane, organic impurities *comprising methyl iodide*, and acid impurities;

reacting the process stream with a basic aqueous solution, the basic aqueous solution comprising water and an alkali metal hydroxide, wherein a concentration of the alkali metal hydroxide in the basic aqueous solution is from about 0.01 wt. % to about [0.5 wt. %] *5 wt.*%; *wherein a temperature of the process stream is from about 5° C. to about 80° and a pressure of the process stream is from about 1 psig to about 100 psig; and a concentration of the methyl iodide in the process stream, in GC area % of total organic compounds, is reduced by at least about 5%;* and separating at least some of the organic impurities from the process stream.

15. The method of claim 14, wherein the alkali metal hydroxide includes potassium hydroxide.

[16. The method of claim 14, wherein in the reacting step, a temperature of the process stream is from about 5° C. to about 80° C. and a pressure of the process stream is from about 1 psig to about 100 psig.]

17. The method of claim 14, wherein [in the providing step, the organic impurities include methyl iodide, and a] *the* concentration of the methyl iodide in the process stream, in GC [area %] *area*% of total organic compounds, is reduced by from about [1%] *5*% to about 70% by the reacting step.

18. The method of claim 14, further comprising an additional step of drying to remove at least some of the water from the process stream immediately after the reacting step.

19. The method of claim 18, wherein after the reacting step, the drying step, and the separation step, the process stream includes at least about 99 wt. % trifluoroiodomethane, less than about 50 ppm methyl iodide, less than about 100 ppm water, and less than about 20 ppm acid impurities.

*20. The method of claim 14, wherein a concentration of the alkali metal hydroxide in the basic aqueous solution is from about 0.01 wt.% to about 2 wt.%.*

*21. The method of claim 14, wherein a concentration of the alkali metal hydroxide in the basic aqueous solution is from about 0.01 wt.% to about 1 wt.%.*

*22. The method of claim 14, wherein a concentration of the alkali metal hydroxide in the basic aqueous solution is from about 0.01 wt.% to about 0.5 wt.%.*

*23. The method of claim 14, wherein a concentration of the alkali metal hydroxide in the basic aqueous solution is from about 0.1 wt.% to about 5 wt.%.*

*24. The method of claim 14, wherein a concentration of the alkali metal hydroxide in the basic aqueous solution is from about 0.1 wt.% to about 2 wt.%.*

*25. The method of claim 14, wherein a concentration of the alkali metal hydroxide in the basic aqueous solution is from about 0.1 wt.% to about 1 wt.%.*

*26. The method of claim 14, wherein a concentration of the alkali metal hydroxide in the basic aqueous solution is from about 0.1 wt.% to about 0.5 wt.%.*

* * * * *